(12) United States Patent
Maity et al.

(10) Patent No.: US 9,453,806 B2
(45) Date of Patent: Sep. 27, 2016

(54) METHOD AND DEVICE FOR DISSOLVED GAS ANALYSIS

(71) Applicant: General Electric Company, Schenectady, NY (US)

(72) Inventors: Sandip Maity, Bangalore Karnataka (IN); Nagapriya Kavoori Sethumadhavan, Bangalore (IN); Samhitha Palanganda Poonacha, Bangalore Karnataka (IN); Prashanth Raghavendra Prasad, Bangalore Karnataka (IN)

(73) Assignee: General Electric Company, Schenectady, NY (US)

( * ) Notice: Subject to any disclaimer, the term of this patent is extended or adjusted under 35 U.S.C. 154(b) by 336 days.

(21) Appl. No.: 14/134,525

(22) Filed: Dec. 19, 2013

(65) Prior Publication Data

US 2014/0165704 A1 Jun. 19, 2014

(30) Foreign Application Priority Data

Dec. 19, 2012 (IN) .......................... 5318/CHE/2012

(51) Int. Cl.
*G01N 33/28* (2006.01)
*G01N 25/00* (2006.01)
*G01N 21/3504* (2014.01)

(52) U.S. Cl.
CPC ......... *G01N 25/005* (2013.01); *G01N 21/3504* (2013.01); *G01N 33/2841* (2013.01)

(58) Field of Classification Search
CPC .................... G01N 33/2841; G01N 21/3504; G01N 2021/3181; G01N 21/359; G01N 33/14; G01N 33/2823; G01N 33/2835
See application file for complete search history.

(56) References Cited

U.S. PATENT DOCUMENTS

| 2,972,251 A | * | 2/1961 | Harper | G01V 8/02 250/253 |
| 4,764,343 A | * | 8/1988 | Nyberg | F02D 41/1451 356/445 |
| 4,890,478 A | * | 1/1990 | Claiborne | G01N 33/2841 73/19.11 |
| 5,062,292 A | * | 11/1991 | Kanba | G01N 33/2841 73/19.01 |
| 5,258,310 A | * | 11/1993 | Abe | G01N 33/2835 436/175 |
| 5,317,156 A | * | 5/1994 | Cooper | G01N 21/39 250/339.13 |
| 5,468,962 A | * | 11/1995 | Ohishi | G01N 21/37 250/343 |
| 6,121,627 A | * | 9/2000 | Tulip | G01N 21/39 250/343 |

(Continued)

OTHER PUBLICATIONS

European Search Report and Written Opinion issued in connection with corresponding EP Application No. 13196659.0-1554 on Jul. 9, 2014.

(Continued)

*Primary Examiner* — David A Rogers
(74) *Attorney, Agent, or Firm* — Parks IP Law LLC; Stephen J. Terrell

(57) ABSTRACT

A system, comprising at least one source for irradiating electromagnetic radiation into a sample fluid and a reference fluid resulting in a change in a temperature of the sample fluid and a change in a temperature of the reference fluid, and a processing subsystem that monitors and determines a concentration of a gas of interest dissolved in the sample fluid based upon a difference between the change in the temperature of the sample fluid and the change in the temperature of the reference fluid, wherein the reference fluid does not contain the gas of interest, and the electromagnetic radiation has a wavelength range corresponding to a spectral absorption range of the gas of interest.

20 Claims, 7 Drawing Sheets

(56) References Cited

U.S. PATENT DOCUMENTS

| | | | | |
|---|---|---|---|---|
| 6,138,497 | A * | 10/2000 | Nix | G01N 7/14 250/339.13 |
| 6,192,737 | B1 * | 2/2001 | Ohlrogge | G01N 7/10 261/104 |
| 6,612,156 | B1 * | 9/2003 | Hakimuddin | B01F 3/1242 73/597 |
| 6,775,001 | B2 * | 8/2004 | Friberg | G01J 3/42 356/432 |
| 7,067,323 | B2 * | 6/2006 | Veale | G01N 21/59 250/343 |
| 7,235,054 | B2 * | 6/2007 | Eckerbom | G01N 21/3504 422/84 |
| 7,456,969 | B2 * | 11/2008 | Chabanis | B64D 37/32 250/341.4 |
| 7,948,626 | B2 * | 5/2011 | Tondello | G01L 11/02 1/2 |
| 8,032,311 | B2 * | 10/2011 | DiFoggio | E21B 47/101 250/256 |
| 8,081,313 | B2 * | 12/2011 | Lam | G01N 21/783 356/436 |
| 8,442,775 | B2 * | 5/2013 | Santos | G01N 33/2841 702/182 |
| 9,003,865 | B2 * | 4/2015 | Takamoto | G01N 33/2841 73/19.09 |
| 9,041,920 | B2 * | 5/2015 | Mander | G01N 21/01 356/51 |
| 9,157,311 | B2 * | 10/2015 | Pelletier | E21B 49/10 |
| 9,176,107 | B2 * | 11/2015 | Jeffrey | G01N 33/2841 |
| 2005/0269499 | A1 * | 12/2005 | Jones | B08B 7/028 250/269.1 |
| 2006/0139646 | A1 * | 6/2006 | DiFoggio | E21B 49/10 356/436 |
| 2011/0246088 | A1 * | 10/2011 | Santos | G01N 33/2841 702/24 |
| 2012/0290208 | A1 * | 11/2012 | Jiang | G01N 21/3504 702/8 |

OTHER PUBLICATIONS

Jakob, "Dissolved Gas Analysis—Past, Present and Future", Weidmann—ACTI Inc., pp. 1-8, Jan. 1, 2003.
Keranen et al., "Differential photo-acoustic gas cell based on LTCC for ppm gas sensing", Proceedings of SPIE, vol. No. 7607, pp. 1-12, Feb. 3, 2010.
Yun et al., "Infrared absorption properties analysis of dissolved gases in transformer oil", 2010 International Conference on Power System Technology, pp. 1-6, Oct. 1, 2010.

* cited by examiner

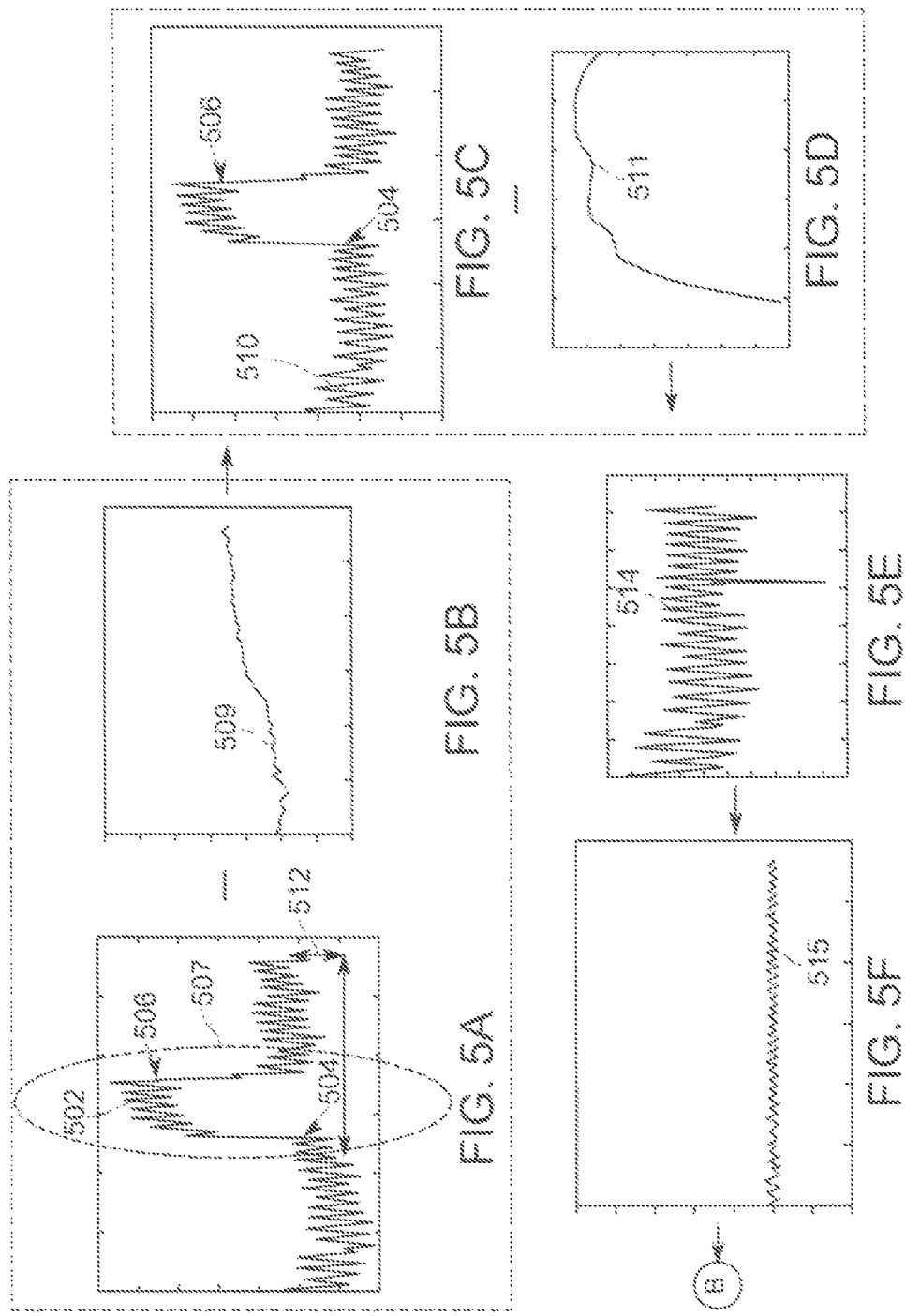

METHOD AND DEVICE FOR DISSOLVED GAS ANALYSIS

TECHNICAL FIELD

The subject matter disclosed generally relates to measuring and testing of dissolved gases, and more specifically to a method and apparatus for selectively detecting and monitoring dissolved gases in a fluid, such as transformer oil.

BACKGROUND

Electrical equipment, particularly medium-voltage or high-voltage electrical distribution equipment, typically requires a high degree of electrical and thermal insulation between components. Accordingly, it is well known to encapsulate components of electrical equipment, such as coils of a transformer, in a containment vessel and to fill the containment vessel with a fluid. The fluid facilitates dissipation of heat generated by the components and can be circulated through a heat exchanger to efficiently lower the operating temperature of the components. The fluid may also serves as electrical insulation between components or to supplement other forms of insulation disposed around the components, such as cellulose paper or other insulating materials. Various fluids having the desired electrical and thermal properties can be used. However, electrical equipment is typically filled with various oils, such as castor oil, mineral oil, and/or a synthetic "oil" such as chlorinated diphenyl or silicone oil.

Often electrical distribution equipment is used in an environment where failure can be very expensive or even catastrophic because of a loss of electric power to critical systems. Also, failure of electrical distribution equipment ordinarily results in a damage to the equipment itself and surrounding equipment, thus requiring replacement. Further, such failure of electrical distribution equipment can cause injury to personnel or other property. Therefore, it is desirable to monitor the status of electrical equipment to predict potential failure of the equipment through detection of incipient faults and to take remedial action through repair, replacement, or adjustment of operating conditions of the equipment.

A known method of monitoring the status of fluid-filled electrical equipment is to monitor various parameters of the fluid. For example, the temperature of the fluid and the total combustible gas (TCG) in the fluid is known to be indicative of the operating state of fluid-filled electrical equipment. Therefore, monitoring these parameters of the fluid can provide an indication of any incipient faults in the equipment. For example, it has been found that carbon monoxide and carbon dioxide increase in concentration with thermal aging and degradation of cellulosic insulation in electrical equipment. Hydrogen and various hydrocarbons (such as acetylene and ethylene, and their derivatives) increase in concentration due to hot spots caused by circulating currents and dielectric breakdown such as corona or arcing. Concentrations of oxygen and nitrogen tend to indicate the quality of the gas pressurizing system employed in large equipment, such as transformers. Accordingly "dissolved gas analysis" (DGA) has become a well-accepted method of discerning incipient faults in fluid-filled electric equipment.

Generally, an amount of fluid is removed from the containment vessel of the equipment through a valve. The removed fluid is then subjected to testing for dissolved gas in a lab or by equipment in the field. This method of testing is referred to herein as "off-line" DGA. Since the gases are generated by various known faults, such as degradation of insulation material or other portions of electric components in the equipment, turn-to-turn discharges in coils, overloading, loose connections, or the like, various diagnostic theories have been developed for correlating the quantities of various gases in fluid with particular faults in electrical equipment in which the fluid is contained.

Known methods of off-line DGA typically require extraction of gases from the fluid for several quantitative analyses. These extracted gases are often analyzed by using photoacoustic spectroscopy or gas chromatography. The gas concentration in the fluid is generally calculated from the measured concentrations of the extracted gases. However, these methods suffer from inaccuracy, uncertainties and repeatability issues generally involved with the complicated extraction process. In addition to this, the gas concentration in liquid is calculated from the measured concentrations of the extracted gases. The calculations have several assumptions involved, leading to errors and uncertainties.

BRIEF DESCRIPTION

These and other drawbacks associated with such conventional approaches are addressed here by providing a system in accordance with various embodiments. The system includes at least one source for irradiating electromagnetic radiation into a sample fluid and a reference fluid resulting in a change in a temperature of the sample fluid and a change in a temperature of the reference fluid, and a processing subsystem that monitors and determines a concentration of a gas of interest dissolved in the sample fluid based upon a difference between the change in the temperature of the sample fluid and the change in the temperature of the reference fluid, wherein the reference fluid does not contain the gas of interest, and the electromagnetic radiation has a wavelength range corresponding to a spectral absorption range of the gas of interest.

In another embodiment, a method is presented. The method includes irradiating a sample fluid and a reference fluid by electromagnetic radiation having a first wavelength range resulting in a first time temperature change of the sample fluid and a first time temperature change of the reference fluid, determining a first difference based upon the first time temperature change of the sample fluid and the first time temperature change of the reference fluid, irradiating the sample fluid and the reference fluid by electromagnetic radiation having a second wavelength range resulting in a second time temperature change of the sample fluid and a second time temperature change of the reference fluid, determining a second difference based upon the second time temperature change of the sample fluid and the second time temperature change of the reference fluid, monitoring and determining a concentration of a gas of interest in the sample fluid based upon the first difference and the second difference.

In still another embodiment, a system is presented. The system includes a first container containing a sample fluid used to determine presence of a gas of interest, a second container containing a reference fluid that does not contain a significant amount of the gas of interest, a source for producing electromagnetic radiation, an optical arrangement that splits the electromagnetic radiations into a first portion of the electromagnetic radiation and a second portion of electromagnetic radiations, and directs the first portion of the electromagnetic radiation into the sample fluid and the second portion into the reference fluid to change the temperature of the sample fluid and change the temperature of the reference fluid, a plurality of sensing devices that generate signals that are representative of the change in the temperature of the sample fluid and the change in the temperature of the reference fluid, a processing subsystem that determines the presence and concentration of the gas of interest in the sample fluid based upon a difference between the change in the temperature of the sample fluid and the change in the temperature of the reference fluid.

A method is presented. The method includes irradiating a sample fluid by electromagnetic radiation having a first wavelength range resulting in a first time temperature change of the sample fluid, irradiating a reference fluid by a second wavelength range resulting in a first time temperature change of the reference fluid, determining a first difference based upon the first time temperature change of the sample fluid and the first time temperature change of the reference fluid, monitoring and determining the concentration of the gas of interest in the sample fluid based upon the first difference.

DRAWINGS

These and other features, aspects, and advantages of the present invention will become better understood when the following detailed description is read with reference to the accompanying drawings, wherein.

Figure 4A:
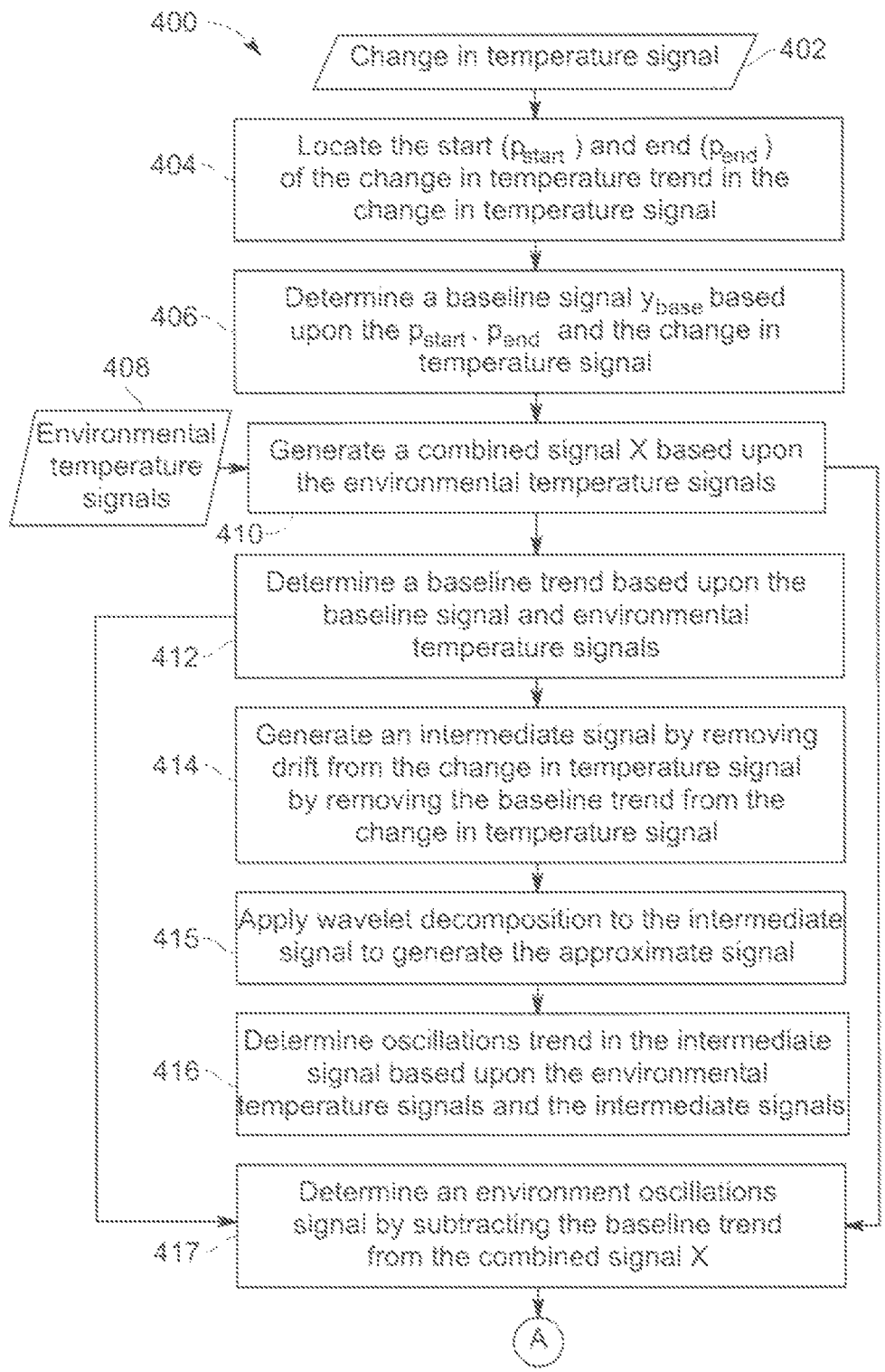
Figure 4B:
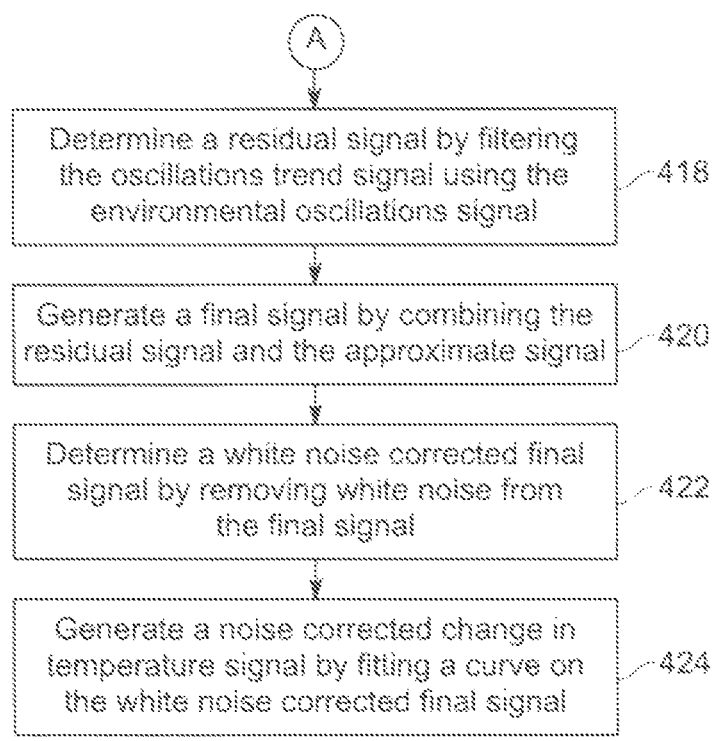
Figure 5I:
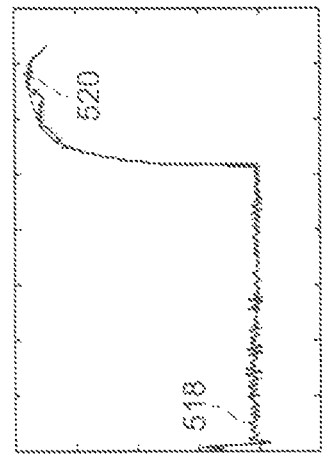
Figure 5G:
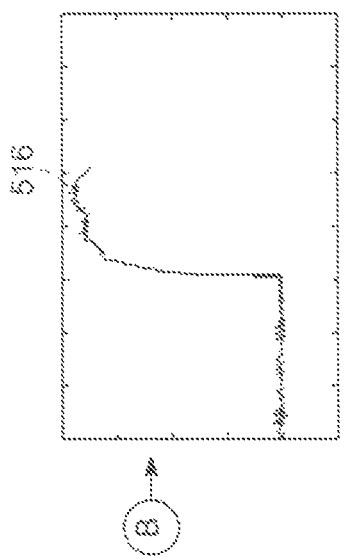
Figure 5H:
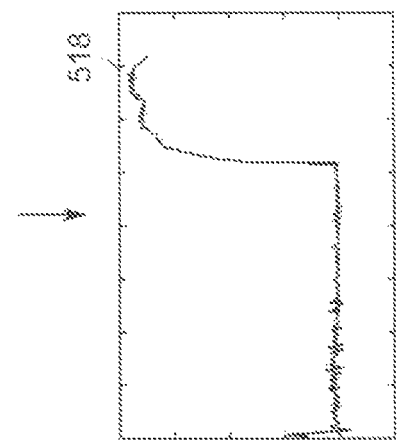

FIG. 4A and FIG. 4B show a flowchart of a method for removing noise signals infused by environment in temperature signals or temperature change signals of a sample fluid or a reference fluid, in accordance with one embodiment of the present techniques; and FIG. 5A, FIG. 5B, FIG. 5C, FIG. 5D, FIG. 5E, FIG. 5F, FIG. 5G, FIG. 5H and FIG. 5I show a group of graphs that show a process for removal of noise signals from a signal that is representative of a difference between a change in the temperature of a sample fluid and a change in the temperature of the reference fluid, in accordance with one embodiment of the present techniques.

DETAILED DESCRIPTION

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. As used herein, the term "and/or" includes any and all combinations of one or more of the associated listed items.

Approximating language, as used herein throughout the specification and claims, may be applied to modify any quantitative representation that could permissibly vary without resulting in a change in the basic function to which it may be about related. Accordingly, a value modified by a term such as "about" is not limited to the precise value specified. In some instances, the approximating language may correspond to the precision of an instrument for measuring the value.

Though the present discussion provides examples in the context of an insulating fluid used in electric power industry, typically in transformers, these processes can be applied to any other fluid or application. In some embodiments, the insulating fluid may include a dielectric or insulating oil, a mineral oil, a coolant, or the like. The method and device described herein may be used with other industries such as chemical industry, petroleum industry, food industry, and water industry. Other suitable examples of the fluid may include vegetable oils, beverages, chemical compounds, or the like.

The present methods and systems measure and test dissolved gases in a fluid, for example transformer oil or cooling fluid. In one embodiment, the present methods and systems determine concentration of the dissolved gases in the fluid. As discussed in detail below, some of the embodiments of the present systems and methods provide for selectively detecting and monitoring dissolved gases in a fluid by using calorimetry without extracting the dissolved gases from the fluid. In one embodiment, the present systems and methods determine the concentration/quantity of dissolved gases in a substantially non-transparent fluid without extracting the dissolved gases.

The present systems and methods monitor a sample fluid to determine the existence or non-existence of one or more dissolved gases in a sample fluid. As used herein, the term "sample fluid" refers to a fluid that is to be monitored and tested to determine the existence or non-existence of a dissolved gas. The present systems and methods further monitor and determine the concentration of the dissolved gases in the sample fluid. The present systems and methods irradiate electromagnetic radiation into the sample fluid and a reference fluid. According to one embodiment, the reference fluid does not contain the dissolved gases. The electromagnetic radiation has wavelengths that correspond to the absorption range of the dissolved gases. In one embodiment, the intensity of the electromagnetic radiation irradiated into the sample fluid and the intensity of the electromagnetic radiation irradiated into the reference fluid is same. The irradiation of the electromagnetic radiation into the sample fluid and the reference fluid may change the temperature of the sample fluid and the reference fluid. The change in the temperatures of the sample fluid and the reference fluid is used to monitor and determine the concentration of the dissolved gases in the sample fluid.

Figure 1:
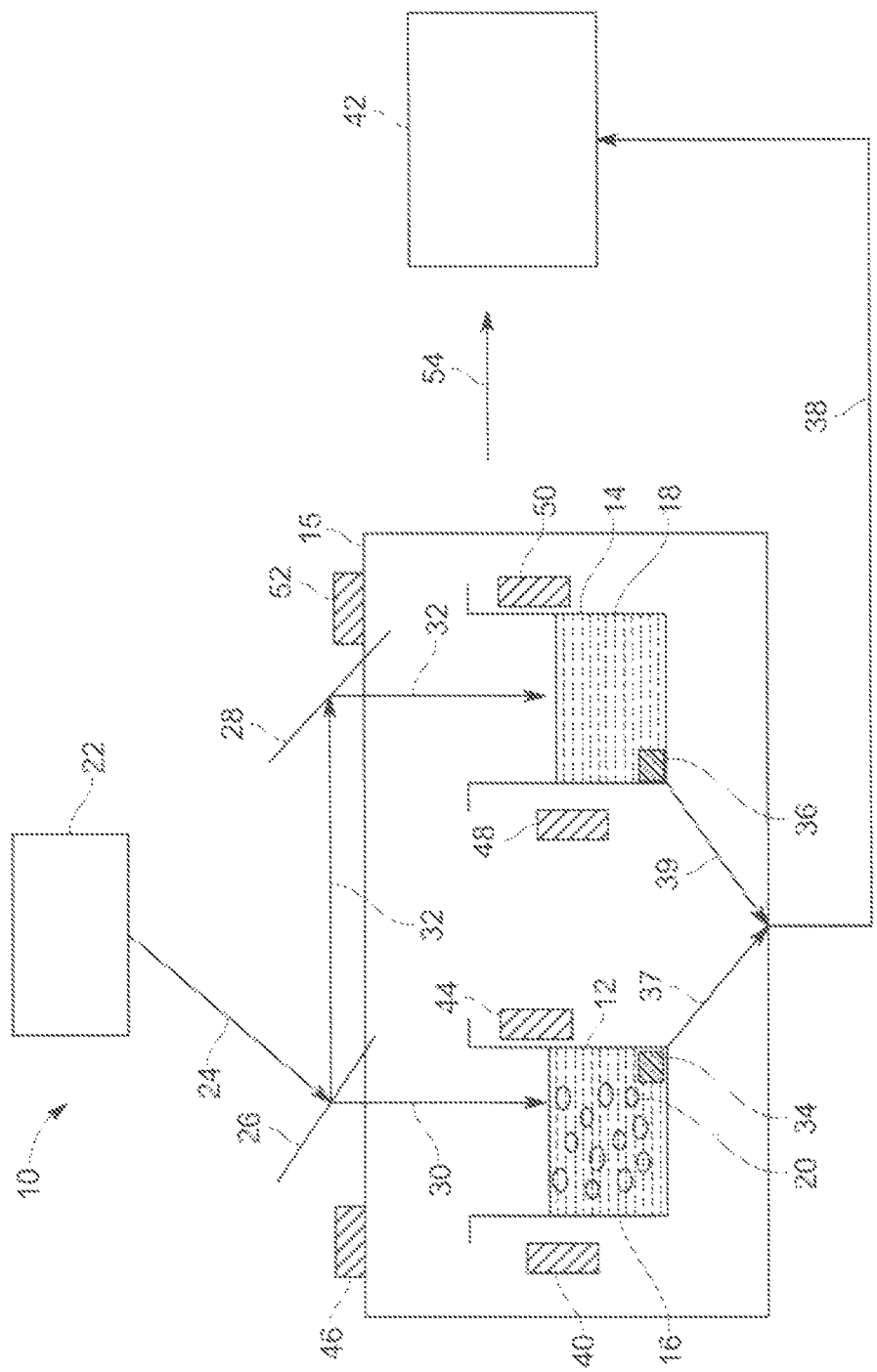
FIG. 1 is a schematic view of a device for monitoring and detecting a dissolved gas or a gas of interest dissolved in a sample fluid, in accordance with an embodiment of the present systems.

A schematic of a device 10 for the detection and monitoring of dissolved gases in fluid is illustrated in FIG. 1 according to one embodiment. The device 10 includes a first container 12 and a second container 14. The first container 12 contains a sample fluid 16, and the second container 14 contains a reference fluid 18. The sample fluid 16, for example, may contain certain dissolved gases of interest. In the presently contemplated configuration, the sample fluid 16 is monitored and tested to determine the presence or concentration of certain dissolved gases. In the presently contemplated configuration, the sample fluid 16 is shown to include certain dissolved gases 20. In one embodiment, the reference fluid 18 does not contain or contains de minimis amount the gas of interest. It is noted that the phrase "reference fluid does not contain gas of interest" means either the reference fluid does not contain the gas of interest or contains minimal amount of the gas of interest that does not affect the spectral absorption properties of the reference fluid. In another embodiment, the reference fluid contains the gas of interest. As used herein, the term "gas of interest" is a gas dissolved in a sample fluid, wherein the sample fluid is monitored to determine the presence and in some cases the concentration of the dissolved gas in the sample fluid. Accordingly, term "a dissolved gas in the dissolved gases 20" and the term "gas of interest" shall be used interchangeably. Furthermore, the sample fluid 16, in one example, is monitored to determine the concentration of the dissolved gases 20. In one embodiment, the sample fluid 16 and the reference fluid 18 is/are substantially non-transparent. In another embodiment, the sample fluid 16 and the reference fluid 18 is/are substantially transparent. In one embodiment, the sample fluid 16 and the reference fluid 18 are substantially same, notwithstanding the reference fluid 18 does not contain the dissolved gases 20. In another embodiment, the sample fluid and reference fluid, are substantially similar notwithstanding the reference fluid 18 does not contain the dissolved gases 20. It is noted that the phrase "reference fluid does not contain gas of interest" means either the reference fluid does not contain the gas of interest or contains minimal amount of the gas of interest that does not affect the spectral absorption properties of the reference fluid. In certain embodiments, the sample fluid 16 and the reference fluid 18 contain the gas of interest 20.

As previously noted, the first container 12 contains the sample fluid 16, and the second container 14 contains the reference fluid 18. The first container 12 and the second container 14 may be of any shape having a volume to contain a sufficient amount of the sample fluid 16 and the reference fluid 18, respectively. The volumes of the containers 12, 14, in one example, are as small as 1 microliter. In some instances, the volumes of the containers 12, 14 may be in a range from about 1 microliter to about 10 milliliters. In some specific instances, the volumes may vary from about 5 microliters to about 5 milliliters. In some specific embodiments, the containers 12, 14 are cylindrical in shape with a cross section area, such as, circular, polygonal, or elliptical in shape. In one embodiment, the volume and size of the second container 14 may be similar to the first container 12. In another embodiment, the volume and size of the first container 12 may be different from the volume and size of the second container 14. In one embodiment, as shown in FIG. 1, the containers 12, 14 may be contained by an outside container 15 that acts as an insulator for the containers 12, 14, and protects the containers 12, 14 from the outside environment. In one embodiment, as shown in FIG. 1, the containers 12, 14 may be contained by the outside container 15 which is temperature controlled and may be used to maintain constant temperature inside it.

As previously noted, in the presently contemplated configuration, while the sample fluid 16 contains the dissolved gases 20, the reference fluid 18 does not contain an appreciable amount of the dissolved gases 20. It is noted that while the reference fluid 18 does not contain the dissolved gases 20, it may contain one or more gases other than the dissolved gases 20. In one embodiment, the dissolved gases 20 may be fault gases. In one embodiment, when the dissolved gases 20 are fault gases, the detection and monitoring of one or more of the dissolved gases 20 may help in detection of faults in an equipment that contains the sample fluid 16 and the fault gases 20. As used herein, "fault gases" refers to gases liberated within equipment upon a fault in the equipment. For example, insulating materials within transformers and related equipment break down to liberate gases. The type and distribution of the liberated gases can be related to the type of electrical fault, and the rate of gas generation or liberation can indicate the severity of the electrical fault. Examples of the fault gases dissolved in the dielectric oil, generally used in transformers, may include one or more dissolved gases such as hydrogen, oxygen, carbon monoxide, carbon dioxide, methane, ethane, ethylene, acetylene, butane, pentane and possibly other species.

Figure 2:
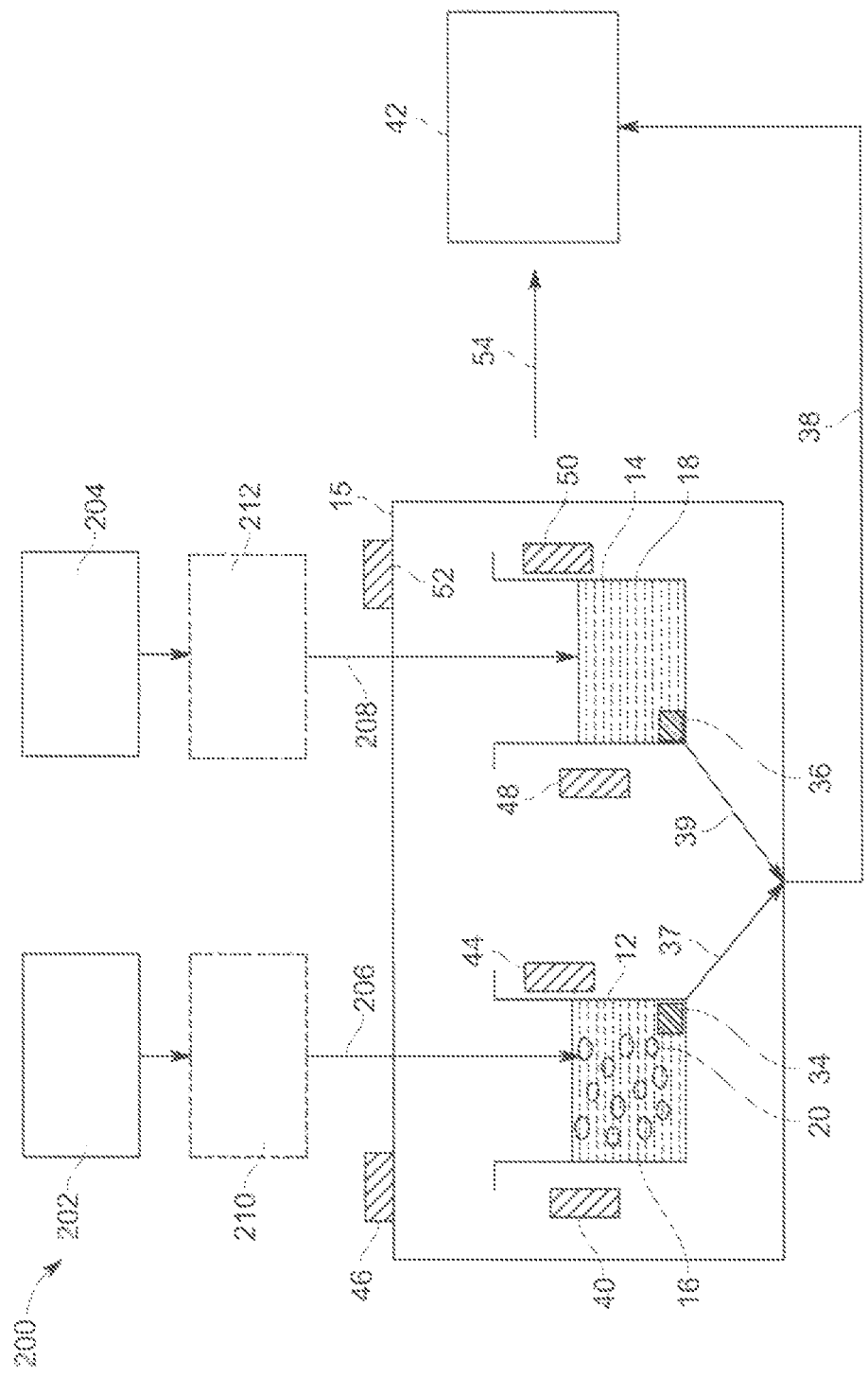
FIG. 2 is a schematic view of another embodiment of the device of FIG. 1 for monitoring and detecting a gas of interest dissolved in the sample fluid, in accordance with another embodiment of the present systems.

As shown in FIG. 1, the system or device 10 further includes a radiation source 22 that produces electromagnetic radiation 24 for detection and monitoring of the dissolved gases 20. In one embodiment, the radiation source 22 may be a laser source. It is noted that while in the presently contemplated configuration, the device 10 includes a single radiation source 22, in certain embodiments; the device 10 may include multiple radiation sources. An embodiment of the device 10 wherein a device includes multiple radiation sources is shown in FIG. 2.

According to one embodiment, the radiation source 22 produces the electromagnetic radiation 24 that has a wavelength range corresponding to the spectral absorption range of the dissolved gases 20. Typically, a fluid may contain several dissolved gases, and in one embodiment, when the device 10 selectively monitors or detects a gas of interest in the dissolved gases 20, the radiation source 22 produces the electromagnetic radiation 24 that has the wavelength range in the spectral absorption range of the gas of interest in the dissolved gases 20. For example, $C_2H_2$ has its fundamental absorption range between about 3200 $cm^{-1}$ to about 3350 $cm^{-1}$, and $CO_2$ has an absorption range between about 2300 $cm^{-1}$ to about 2400 $cm^{-1}$. An absorption range includes absorption lines at several wavelengths, which means that the absorption is higher at particular wavelengths in the range. Examples of particular wavelengths include about 3309.5 $cm^{-1}$ for detecting $C_2H_2$ and about 2325 $cm^{-1}$ for detecting $CO_2$, though, of course, other wavelengths may be suitable for detecting these gases or other gases.

In the illustrated embodiment, the device 10 further includes a beam splitter 26, and a mirror 28. The beam splitter 26, for example, may be located above the first container 12, and the mirror 28 may be located above the second container 14. However, in one embodiment, the beam splitter 28 may be located above the second container 14, and the mirror 28 may be located above the first container 12. The radiation source 22 is disposed at a position to direct the electromagnetic radiation 24 onto the beam splitter 26. In some instances, suitable optical arrangements may be used to direct the radiations 24 onto the beam splitter 26. For example, the electromagnetic radiation 24 may be collected by an aspheric lens and collimated using a lens.

The radiation source 22 transmits the electromagnetic radiation 24 onto the beam splitter 22 that splits the electromagnetic radiation 24 into two portions 30, 32. The two portions 30, 32, for example, include a first portion of electromagnetic radiations 30, and a second portion of electromagnetic radiation 32. In one embodiment, the beam splitter 26 splits the electromagnetic radiation 24 in such a way that the intensity of the first portion of the electromagnetic radiation 30 is similar to the intensity of the second portion of the electromagnetic radiation 32. It is noted that in the present techniques, the intensity of the first portion of the electromagnetic radiation 30 and the intensity of the second portion of the electromagnetic radiation 32 need not be exactly same, notwithstanding that the intensity of the first portion of the electromagnetic radiation 30 and the intensity of the second portion of the electromagnetic radiation 32 may be similar. In one embodiment, intensity in the first portion of the electromagnetic radiation 30 is substantially similar to the intensity in the second portion of the electromagnetic radiation 32 when the intensity in the first portion of the electromagnetic radiation 30 is +10% of the intensity of the second portion of the electromagnetic radiation.

The first portion of the electromagnetic radiation 30 is directed/irradiated into the first container 12 and the second portion of the electromagnetic radiation 32 is directed/irradiated onto a mirror 28. The mirror 28 reflects and directs the second portion of the electromagnetic radiation 32 into the second container 14. Therefore, the first portion of the electromagnetic radiation 24 is directed/irradiated into the first container 12 that contains the sample fluid 16, and the second portion of the electromagnetic radiation 32 is directed into the second container 14 that contains the reference fluid 18. In this example, the first portion of the electromagnetic radiation 30 and the second portion of the electromagnetic radiation 32 are simultaneously irradiated/directed into the sample fluid 16 and the reference fluid 18.

In the presently contemplated configuration, the direction of the first portion of the electromagnetic radiation 30 into the first container 16 changes the temperature of the sample fluid 16 contained in the first container 12. The temperature of the sample fluid 16 changes due to absorption of the first portion of the electromagnetic radiation 30 by the dissolved gases 20 and by the sample fluid 16. In an ideal condition, since the first portion of the electromagnetic radiation 30 has the wavelength range that correspond to the spectral absorption range of the dissolved gases 20, only the dissolved gases 20 absorb the first portion of the electromagnetic radiation 30 to change the temperature of the sample fluid 16. In ideal conditions, when only the dissolved gases 20 in the sample fluid 16 absorb the first portion of the electromagnetic radiation 30, the absorption of the first portion of the electromagnetic radiation 30 by the dissolved gases 20 changes the temperature of the sample fluid 16. However, due to various factors, such as, non-transparency of the sample fluid 16, properties of the sample fluid 16, some of the first portion of the electromagnetic radiation 30 may be absorbed by the sample fluid 16 and by the dissolved gases 20 to change the temperature of the sample fluid 16. Accordingly, in such conditions, the change in the temperature of the sample fluid 16 is due to the change in the temperature of the sample fluid 16 and the dissolved gases 20. In the presently contemplated configuration, the change in the temperature is an increase in temperature. Particularly, the change in the temperature may be apparent heating up of the sample fluid 16 in the first container 12. In some other cases, the sample fluid+dissolved gas could absorb the electromagnetic radiation and undergo some chemical change which could possibly cause a decrease in temperature.

Furthermore, the irradiation of the second portion of the electromagnetic radiation 32 into the second container 14 may change the temperature of the reference fluid 18 contained in the second container 14. In ideal conditions, since the second portion of the electromagnetic radiation 32 has the wavelength range that correspond to the spectral absorption range of the dissolved gases 20, the reference fluid 18 in the second container 14 does not absorb the second portion of the electromagnetic radiation 32. However, due to factors, such as, non-transparency of the reference fluid 18, properties of the reference fluid 18, existence of gases other than the dissolved gases 20, the reference fluid 18 and/or the gases other than the dissolved gases 20 may absorb some of the second portion of the electromagnetic radiation 32. The absorption of the second portion of the electromagnetic radiation 32 by the reference fluid 18 and/or the gases other than the dissolved gases 20 may change the temperature of the reference fluid 18. In the presently contemplated configuration, the change in the temperature of the reference fluid is an increase in the temperature of the reference fluid 18.

In one example, the device 10 further includes one or more temperature sensors 34, 36 that measure the change in temperatures of the sample fluid 16 and the reference fluid 18, respectively to generate signals 37, 39. The signal 37 is representative of the change in the temperature of the sample fluid 16 and the signal 39 is representative of the change in the temperature of the reference fluid 18. In some specific embodiment, the temperature sensors 34, 36 are located in the containers 12, 14 as shown in FIG. 1. One or more of the temperature sensors 34, 36, for example, may be an electrical sensor or an optical sensor. In some embodiments, one or more of the temperature sensors 34, 36 may be a linear temperature sensor. Suitable examples of the electrical temperature sensors 34, 36 include thermocouples, resistive temperature detectors (for example Pt100, Pt1000), thermistors, semiconductor sensors or diodes. Some example of optical temperature sensing techniques include surface plasmon resonance (SPR), and interferometry. Criteria and tradeoffs for selecting a sensor type or types from among the available options for a given situation will be apparent to those skilled in the art.

Hereinafter, the term "temperature sensor 34" shall be referred to as "first temperature sensor 34." Hereinafter, the term "temperature sensor 36" shall be referred to as "second temperature sensor 36." In the presently contemplated configuration, the first temperature sensor 34 is located inside the first container 12 and the second temperature sensor 36 is located inside the second container 14. Resolution of the temperature sensors 34, 36 may vary case by case. In some embodiments, the temperature sensors 34, 36 with high resolution, for example 20 micro kelvin may be desirable. In some embodiments, the temperature sensors 34, 36 with lower resolution may be sufficient for the temperature measurement. In some embodiments, the temperature sensor may have resolution between about 20 micro kelvin and about 10 kelvin. One skilled in art knows to use a suitably sensitive temperature sensor according to the expected range of the change in temperature of the fluid for a particular gas.

In one embodiment, the first container 12 includes the first sensor 34, and the second container 14 includes the second sensor 36, wherein the sensors 34, 36 are arranged in a differential measurement arrangement. For example, the differential measurement arrangement may be a Wheatstone bridge or any other differential measurement arrangement. The differential measurement arrangement generates signals 38 that are representative of a difference between the change in the temperature of the sample fluid 16 and the change in the temperature of the reference fluid 18 due to irradiation of the first portion of the electromagnetic radiation into the sample fluid and the second portion of the electromagnetic radiation into the reference fluid. The signals 38 that are representative of the difference between the change in the temperature of the sample fluid 16 and the change in the temperature of the reference fluid 18 may be generated based upon the signals 37, 39. Accordingly, in one embodiment, when the change in temperature of the sample fluid 16 due to irradiation of the electromagnetic radiation 30 is $\Delta T_{sample}$ and the change in temperature of the reference fluid 18 due to irradiation of the electromagnetic radiation 32 is $\Delta T_{ref}$, then the differential measurement arrangement or the Wheatstone bridge generates signals 38 that are representative of the difference between the change in temperature signals of the sample fluid 14 and the reference fluid 16, which may be represented as follows:

$$\Delta T = \Delta T_{sample} - \Delta T_{ref} \quad (1)$$

In certain embodiments, the device 10 further includes a processing subsystem 42 that is in operational communication with the first temperature sensor 34 and the second temperature sensor 36 and the device 10. It is noted that while in the presently contemplated configuration, the processing subsystem 42 receives the signals 38 representative of the difference between the change in temperature of the sample fluid 14 and the change in the temperature of the reference fluid 16, in certain embodiments, the processing subsystem 42 may receive the temperatures of the sample fluid 16 and the reference fluid 18 from the sensors 34, 36, and determine a difference between the change in temperature signals based upon the temperatures of the sample fluid 16 and the reference fluid 18.

Irradiation of electromagnetic radiation into the sample fluid 16 and/or the reference fluid 18 may lead to absorption of the electromagnetic radiation 30, 32 by the sample fluid 16, the reference fluid 18 and the dissolved gases 20. The absorption of the electromagnetic radiation 30, 32 may result in conduction, convection and radiation heat gain by the sample fluid 16 and/or the reference fluid 18 to increase the temperature of the sample fluid 16 and/or the reference fluid 18. The increase in the temperature of the sample fluid 16 and/or the reference fluid and/or the difference in temperature between the sample and reference fluids may be very small, for example, in the range of micro Kelvin (~μK). The temperature of surrounding environment may introduce temperature error (hereinafter, referred to as noise) in the signals 38 (see FIG. 1). Considering that the temperature change in the sample fluid 16 and/or the reference fluid 18 and/or the difference in temperature between the sample and reference fluids may be in the range of micro Kelvin (~μK), the noise tends to mask the temperature change leading to inaccurate decisions on the existence and/or the concentration of the dissolved gases 20. The noise, for example, may be in the form of drift and/or oscillations in the signals 38. Therefore, it is advantageous to remove the noise introduced in the signals 37, 39, 38 due to the environmental effects.

To remove the noise signals from the signals 38, the device 10, may further include a plurality of environmental sensors 40, 44, 46, 48, 50, 52. As used herein, the term "environmental sensors" refers to sensors that measure temperature of the nearby environment of the first container 12 and the second container 14. In accordance with one embodiment, the environmental sensors 40, 44, 46, 48, 50, 52 may be located proximate the containers 12, 14 as shown in FIG. 1. The environmental sensors 40, 44, 46, 48, 50, 52 may be located outside the containers 12, 14, and at locations other than the ones shown in FIG. 1. In the presently contemplated configuration, the environmental sensors 40, 44, 46 are located proximate the environment of the first container 12. The environmental sensors 40, 44, 46 measure the temperature of nearby environment of the first container 12. Similarly, the environmental sensors 48, 50, 52 are located in the nearby environment of the second container 14. The environmental sensors 48, 50, 52 measure the temperature of the nearby environment of the second container 14. The environmental sensors 40, 44, 46, 48, 50, 52 measure the temperature of the nearby environment of the first container 12 and the second container 14 to generate environmental temperature signals 54 that are representative of the temperatures of the nearby environment of the first container 12 and the second container 14.

As shown in FIG. 1, the environmental sensors 40, 44, 46, 48, 50, 52 are in an operational communication with the processing subsystem 42. The processing subsystem 42 receives the environmental temperature signals 54 that are representative of temperature of the nearby environment of the first container 12 and the second container 14. The processing subsystem 42 further removes the effects of environment temperature on the change in the temperature of the sample fluid 16 and the reference fluid 18 using the environmental temperature signals 54. In one embodiment, the processing subsystem 42 removes noise introduced in the signals 37, 39 before determining the concentration of the dissolved gases 20 in the sample fluid 16. In one embodiment, the processing subsystem 42 removes noise introduced in the signal 38 before determining the concentration of the dissolved gases 20 in the sample fluid 16. Particularly, the processing subsystem 42 eliminates drift and reduces oscillations introduced in the signals 37 and 39, or in the difference signal 38 due to environmental temperature. The removal of the effects of the environment temperature on the signals 37, 38, 39 is explained in greater detail with reference to FIG. 4.

Subsequent to the generation of the signals 38 representative of the difference between the change in temperature of the sample fluid 16 and the change in the temperature of the reference fluid 18, and the removal of the noise signals from the signals 38, the processing subsystem 42 identifies, monitors and/or determines the dissolved gases 20 based upon the signals 38. In one embodiment, the processing subsystem 42 determines the concentration of the dissolved gases 20 in the sample fluid 16 based upon the difference between the change in temperature of the sample fluid 16 and the change in temperature of the reference fluid 18. In another embodiment, the processing subsystem 42 determines the concentration of the dissolved gases based upon the difference between the change in temperature of the sample fluid 16, the change of temperature of the reference fluid 18 and a calibration constant. In one embodiment, the calibration constant may be determined experimentally. In another embodiment, the calibration constant, for example, may be determined based upon the extinction coefficient of the dissolved the gas of interest, length of the first container 12, the input intensity and the thermal resistance between the first container and the environment. The monitoring and determination of the concentration of the dissolved gases 20 in the sample fluid 16 is explained in greater detail with reference to FIG. 3.

Referring now to FIG. 2, a system or device 200 that includes two radiation sources 202, 204 is shown. The device 200, for example, shows another embodiment of the device 10 referred to in FIG. 1. In the presently contemplated configuration, the device 200 includes the first radiation source 202 and the second radiation source 204. The first radiation source 202 and the second radiation source 204, for example, may be similar to the radiation source 22 (see FIG. 1). A variety of radiation sources 22, 202, 204 (see FIG. 1 and FIG. 2) may be used, including ionizing and non-ionizing radiation sources, which may emit coherent radiation. The radiation sources 22, 202, 204 may emit radiation having wavelength in a range from near infra-red to mid infrared region. Suitable examples may include thermal radiation sources, LED sources, MEMS sources, and incandescent lamps. In one embodiment, the radiation sources 22, 202, 204 is a laser source that is monochromatic, and provides a narrow wavelength band sometimes referred to as a coherent electromagnetic field. In some instances, a tunable diode laser (TDL) may be used as it can be tuned or set to produce radiation at individual wavelengths to detect and monitor several gases individually in the fluid. In addition, the TDL can also be set to produce and monitor different absorption lines for the same gas for confirmation and accuracy. In some instances, a quantum cascade laser (QCL) can be used as the source due to its ability to produce radiation of wavelengths in the mid IR range, and due to its tunable nature and its narrow line width can be used to monitor the hyperfine lines in the gas spectrum.

In the presently illustrated configuration, the first radiation source 202 and the second radiation source 204 produce electromagnetic radiation 206, 208, respectively, having wavelengths that correspond to the spectral absorption range of the dissolved gases 20 in the sample fluid 16. In one embodiment, when a gas of interest in the dissolved gases 20 is monitored, or when a concentration of the gas is determined, the first radiation source 202 and the second radiation source 204 may produce the electromagnetic radiation 206, 208 that have wavelengths within an absorption range of the gas of interest in the dissolved gases 20.

The first radiation source 202, for example, may be located at a position, such that the first radiation source 202 directs the electromagnetic radiation 206 into the sample fluid 16 in the first container 12. Similarly, the second radiation source 204 may be located at a position such that the electromagnetic radiation 208 is directed into the reference fluid 18 in the second container 14. It is noted that in the presently contemplated configuration, the device 200 does not include the beam splitter 26 and the mirror 28 referred to in FIG. 1 due to the existence of the two radiation sources 202, 204 that transmit the electromagnetic radiation 206, 208 into the first container 12 and the second container 14, respectively. In one embodiment, the device 200 may include suitable optical arrangements 210, 212 to direct the electromagnetic radiation 206, 208 into the first container 12 and the second container 14, respectively. The optical arrangements or elements can be used to filter, collimate or otherwise condition the electromagnetic radiation 206, 208 from the radiation sources 202, 204. The first radiation source 202 transmits electromagnetic radiation 206 into the first container 12, and the second radiation source 202 transmits electromagnetic radiation 208 into the second container 14. In one embodiment, the intensity of the electromagnetic radiation 206 is similar to the intensity of the electromagnetic radiation 208. The rest of the components and functionalities of the device 200 in FIG. 2 remains similar to the components and functionalities of the device 10 explained with reference to FIG. 1.

Figure 3:
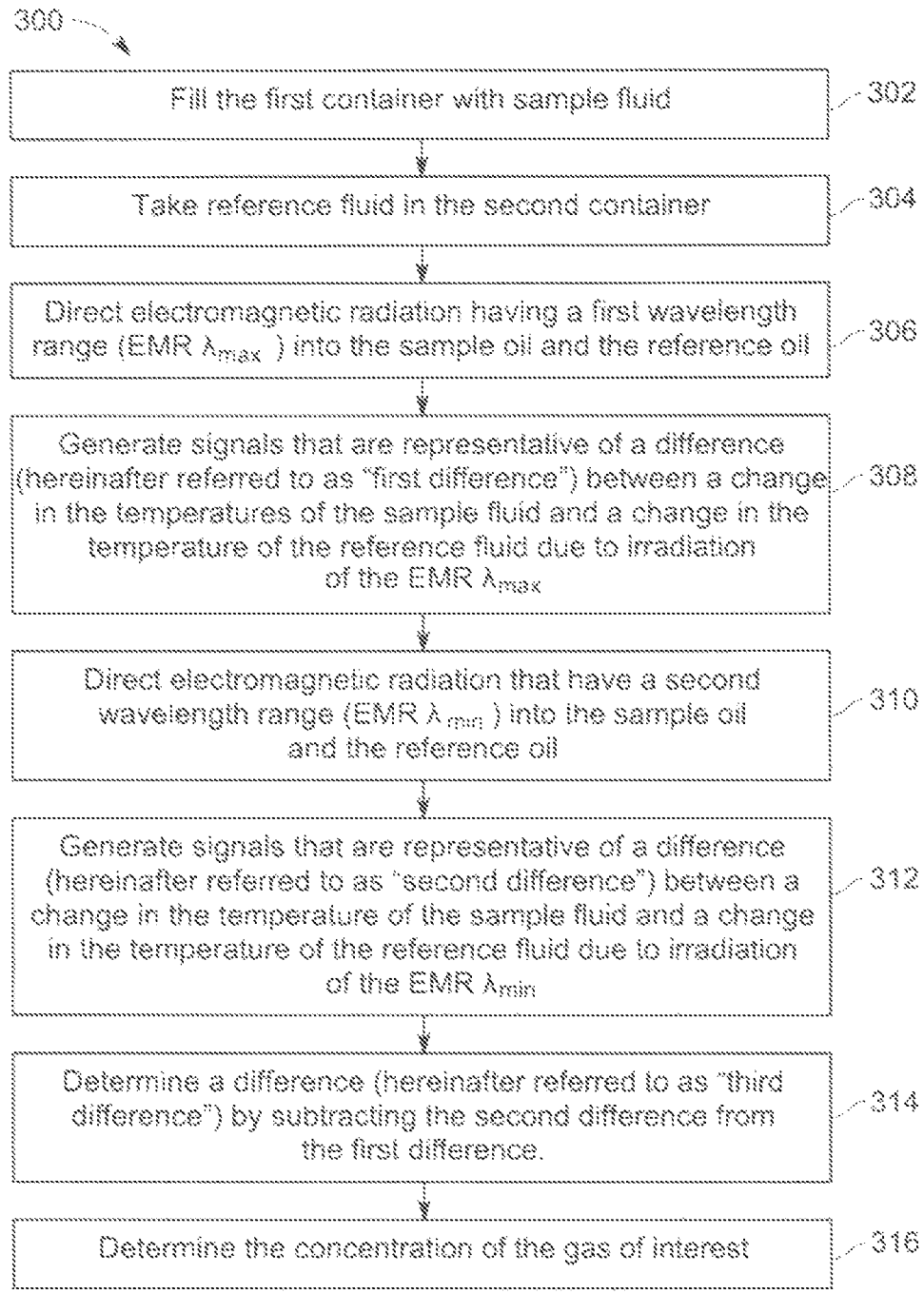
FIG. 3 is a flowchart of a method for determination of the existence or a non-existence of a gas of interest dissolved in the sample fluid, in accordance with one embodiment of the present techniques.

Referring now to FIG. 3, a flowchart of a method 300 for determination of the existence or non-existence of a gas of interest dissolved in a sample fluid is explained in accordance with one embodiment of the present techniques. The sample fluid, for example, may be the sample fluid 16 referred to in FIG. 1. In the presently contemplated configuration, the sample fluid is tested to determine the presence and concentration (if present) of the gas of interest in the sample fluid. As previously noted with reference to FIG. 1, the term "gas of interest" refers to a gas dissolved in a sample fluid, wherein the sample fluid is monitored to determine the existence or non-existence, and concentration of the gas dissolved in the sample fluid. As shown in FIG. 3, at 302, the sample fluid is filled in the first container 12 (see FIG. 1). In the presently contemplated configuration, the sample fluid is oil. The sample fluid may or may not contain the gas of interest. The gas of interest, for example, may be one of the dissolved gases 20 (see FIG. 1).

Further, at 304, a reference fluid is filled in the second container 14. In the presently contemplated configuration, the reference fluid is oil. In one embodiment, the reference fluid is substantially same as the sample fluid. In another embodiment, the reference fluid is substantially similar to the sample fluid. It is noted that notwithstanding the reference fluid being substantially same as the sample fluid or being substantially similar to the sample fluid, the reference fluid does not contain the gas of interest. In one embodiment, the reference fluid may contain the gas of interest.

At 306, electromagnetic radiation that has a first wavelength range are directed into the sample fluid and the reference fluid. In one example, the first wavelength range includes wavelengths of the electromagnetic radiation that correspond to spectral absorption peak of the gas of interest. The first wavelength range, for example, may be determined based upon the specific gas absorption spectral databases or experimentally by using absorption spectroscopy. For example, for a gas of interest CO, one spectral absorption peak is at $2150.8$ $cm^{-1}$ and a spectral absorption valley is at $2152.6$ $cm^{-1}$. Hereinafter, the electromagnetic radiation that has the first wavelength range will be referred to as EMR $\lambda_{max}$. It is noted that while a first portion of the EMR $\lambda_{max}$ is irradiated into the sample fluid and a second portion of the EMR $\lambda_{max}$ is irradiated into the reference fluid, for ease of understanding the discussion hereinafter will refer to irradiation of both fluid by the EMR $\lambda_{max}$, and shall not refer to the irradiation of the first portion of the EMR $\lambda_{max}$ and the second portion of the EMR $\lambda_{max}$.

As previously noted with reference to FIG. 1, the irradiation EMR $\lambda_{max}$ may result in an increase in the temperature of the sample fluid and the reference fluid. In some embodiments, when the sample fluid is substantially transparent and does not contain the gas of interest, the EMR $\lambda_{max}$ may not be absorbed by the sample fluid, and therefore does not change the temperature of the sample fluid. Therefore, in certain embodiments, the change in temperature of the sample fluid due to the irradiation of the electromagnetic radiation $\lambda_{max}$ may be approximately zero. When the change in the temperature of the sample fluid is zero, it may be deduced, that the sample fluid does not contain a sufficient level of the gas of interest. Similarly, in certain embodiments, when the reference fluid is substantially transparent, the EMR $\lambda_{max}$ may not be absorbed by the reference fluid, and therefore, the change in the temperature of the reference fluid is approximately zero. In alternative embodiments, when the sample fluid is substantially non-transparent, and the sample fluid contains the gas of interest, the EMR $\lambda_{max}$ is absorbed by the sample fluid and the gas of interest to change the temperature of the sample fluid. Similarly, when the reference fluid is substantially non-transparent, some of the EMR $\lambda_{max}$ is absorbed by the reference fluid to change the temperature of the reference fluid. In certain alternative embodiments, when the sample fluid is substantially non-transparent and the sample fluid does not contain the gas of interest, the sample fluid may absorb some of the EMR $\lambda_{max}$ to change the temperature of the sample fluid.

The phrase "change in the temperature of the sample fluid due to irradiation of the EMR $\lambda_{max}$" hereinafter shall be interchangeably used with the phrase "first time temperature change of the sample fluid". Similarly, hereinafter, the phrase "change in the temperature of the reference fluid due to irradiation of the EMR $\lambda_{max}$" shall be interchangeably used with the phrase "first time temperature change of the reference fluid". Subsequently at 308, signals that are representative of a difference between the change in temperature of the sample fluid and the change in temperature of the reference fluid due to irradiation of the EMR $\lambda_{max}$ are generated. In other words, signals that are representative of a difference between the first time temperature change of the sample fluid and the first time temperature change of the reference fluid are generated. The signals, for example may be the signals 38 (see FIG. 1). In one embodiment, signals that are representative of the difference between the change in temperature of the sample fluid and the change in the temperature of the reference fluid are generated by a differential arrangement of the first container and the second container based upon the temperature detected by the sensors 34, 36 (see FIG. 1). In another embodiment, the signals that are representative of a difference between the change in temperature of the sample fluid and the change in the temperature of the reference fluid is determined by the processing subsystem 42 based upon the signals generated by the sensors 34, 36 (see FIG. 1). Hereinafter, the phrase "the difference between the change in temperature of the sample fluid and the change in the temperature of the reference fluid due to irradiation of the EMR $\lambda_{max}$" will be referred to as first difference. The first difference for, example, may be represented by the following equation (2):

$$\Delta T_1 = \Delta T_{sample(1)} - \Delta T_{ref(1)} \qquad (2)$$

where $\Delta T_1$ is a first difference, $\Delta T_{sample(1)}$ is the first time temperature change of the sample fluid, $\Delta T_{ref(1)}$ is the first time temperature change of the reference fluid. In one embodiment, the first difference may be represented by the following equation (3):

$$\Delta T_1 = (\Delta T_{sample(1)} - \Delta T_{ref(1)}) \sim \exp(-\beta_{ref\text{-}oil} L_{ref}) - \exp(-(\alpha_{gas} c_{gas} + \beta_{sample\text{-}oil}) L_{sample})$$

wherein $\alpha_{gas}$ refers to an extinction coefficient of a gas of interest, $c_{gas}$ represents the concentration of the gas of interest in the sample fluid, $\beta_{sample\text{-}oil}$ represents absorption coefficient of the sample fluid, $\beta_{ref\text{-}oil}$ represents absorption coefficient of the reference fluid, $L_{sample}$ represents length of path of the EMR $\lambda_{max}$ into the first container 12, and $L_{ref}$ represents length of path of the EMR $\lambda_{max}$ into the second container 14.

It is noted that the $\Delta T_{sample(1)}$ and the $\Delta T_{ref(1)}$, the difference $\Delta T_1$ may be processed to remove noise introduced due to environment temperature before determination of the first difference $\Delta T_1$. The noise, for example, may be removed based upon signals, such as, the signals 54 (see FIG. 1). The removal of noise from $\Delta T_{sample(1)}$ and the $\Delta T_{ref(1)}$ is explained in greater detail with reference to FIG. 4.

At 310, electromagnetic radiation that has a second wavelength range is directed into the sample fluid and the reference fluid. The second wavelength range includes wavelengths of the electromagnetic radiation that correspond to spectral absorption valley of the gas of interest, if present in the sample fluid. For example, for a gas of interest CO, one spectral absorption peak (EMR $\lambda_{max}$) is at 2150.8 cm$^{-1}$ and a spectral absorption valley (EMR $\lambda_{min}$) is at 2152.6 cm$^{-1}$. In another example, for the gas of interest CO, another spectral absorption peak (EMR $\lambda_{max}$) is at 2193.3 cm$^{-1}$ and another spectral absorption valley (EMR $\lambda_{min}$) is at 2195 cm$^{-1}$. A person skilled in the art can identify one or more spectral absorption peaks and one more spectral absorption valleys corresponding to each gas of interest. The second wavelength range, for example, may be determined based upon gas absorption spectral database or experimentally using absorption spectroscopy. Hereinafter, the electromagnetic radiation that has the second wavelength range will be referred to as EMR $\lambda_{min}$. Accordingly, irrespective of the sample fluid and reference fluid being transparent or non-transparent, the gas of interest if present in the sample fluid will not absorb or absorb a substantially minimal amount of the EMR $\lambda_{min}$.

It is noted that the irradiation of the EMR $\lambda_{min}$ may result in an increase in the temperature of the sample fluid and the reference fluid. In some embodiments, when the sample fluid and the reference fluid are substantially transparent (irrespective of the presence or absence of the gas of interest in the sample fluid), the EMR $\lambda_{min}$ may not be absorbed by the sample fluid, and therefore does not change the temperature of the sample fluid. Therefore, in certain embodiments, the change in temperature of the sample fluid and the reference fluid due to the irradiation of the electromagnetic radiation EMR $\lambda_{min}$ may be approximately zero. In alternative embodiments, when the sample fluid and the reference fluid are substantially non-transparent (irrespective of the presence or absence of the gas of interest in the sample fluid), the EMR $\lambda_{min}$ is absorbed by the sample fluid and the reference fluid resulting in a change in the temperature of the sample fluid and the reference fluid, respectively.

Subsequently at 312, signals that are representative of a difference between the change in temperature of the sample fluid and the change in temperature of the reference fluid due to irradiation of the EMR $\lambda_{min}$ are generated. The signals, for example may be the signals 38 (see FIG. 1). In one embodiment, signals that are representative of a difference between the change in temperature of the sample fluid and the change in temperature of the reference fluid due to irradiation of the EMR $\lambda_{min}$ are generated by a differential measurement arrangement of the first container and the second container (see description in FIG. 1). In another embodiment, the signals that are representative of a difference between the change in temperature of the sample fluid and the change in temperature of the reference fluid due to irradiation of the EMR $\lambda_{min}$ are determined by the processing subsystem. The phrase "change in the temperature of the sample fluid due to irradiation of the EMR $\lambda_{min}$" hereinafter shall be interchangeably used with the phrase "second time temperature change of the sample fluid". Similarly, hereinafter, the phrase "change in the temperature of the reference fluid due to irradiation of the EMR $\lambda_{min}$" shall be interchangeably used with the phrase "second time temperature change of the reference fluid". Hereinafter, the phrase "the difference between the change in temperature of the sample fluid and the change in the temperature of the reference fluid due to irradiation of the EMR $\lambda_{min}$ will be referred to as a second difference. The second difference, for example may be represented by the following equation (4):

$$\Delta T_2 = \Delta T_{sample(2)} - \Delta T_{ref(2)} \qquad (4)$$

where $\Delta T_2$ is a second difference, $\Delta T_{sample(2)}$ is a second time temperature change of the sample fluid, and the reference fluid, $\Delta T_{ref(2)}$ is a second time temperature change of the reference fluid due to irradiation of the EMR $\lambda_{min}$. In one embodiment, the second difference may be represented by the following equation (5):

$$\Delta T_2 = (\Delta T_{sample(2)} - \Delta T_{ref(2)}) \sim \exp(-\beta_{ref\text{-}oil} L_{ref}) - \exp(\beta_{sample\text{-}oil}) L_{sample} \qquad (5)$$

wherein $\alpha_{gas}$ gas refers to an extinction coefficient of a gas of interest, $c_{gas}$ represents the concentration of the gas of interest in the sample fluid, $\beta_{sample\text{-}oil}$ represents absorption coefficient of the sample fluid, $\beta_{ref\text{-}oil}$ represents absorption coefficient of the reference fluid, $L_{sample}$ represents length of path of the EMR $\lambda_{min}$ into the first container 12, and $L_{ref}$ represents length of path of the EMR $\lambda_{min}$ into the second container 14. It is noted that the second time temperature change of the sample fluid $\Delta T_{sample(2)}$ and the second time temperature change of the reference fluid $\Delta T_{ref(2)}$, the first difference $\Delta T_1$, or the second difference $\Delta T_2$ may be processed to remove noise introduced due to environmental temperature before determination of the second difference $\Delta T_2$. The noise, for example, may be removed based upon signals, such as, the signals 54 (see FIG. 1). The removal of noise from second time temperature change of the sample fluid $\Delta T_{sample(2)}$ and the second time temperature change of the reference fluid $\Delta T_{ref(2)}$ is explained in greater detail with reference to FIG. 4.

At 314, a third difference may be determined by subtracting the second difference from the first difference. The third difference may be represented by the following equation (6):

$$\Delta T_3 = (\Delta T_1 - \Delta T_2) \sim (\exp(-(\alpha_{gas} c_{gas} + \beta_{sample-oil}) L_{sample}) - \exp(-\beta_{sample-oil} L_{sample})) \quad$$

Furthermore, at 316, the concentration of the gas of interest $c_{gas}$ in the sample fluid may be determined based upon the third difference. The concentration of the gas of interest, for example, may be determined using the following equation (7):

$$\Delta T_3 = (\Delta T_1 - \Delta T_2) \sim \alpha_{gas} c_{gas} L_{sample} \sim c_{gas} \quad (7)$$

In view of the equation (7) it is noted that the concentration of the gas of interest may be determined based upon the first difference, second difference, the extinction coefficient of the gas of interest and the length of the first container.

It is also noted that while FIG. 3 shows irradiation of the sample fluid and the reference fluid by the electromagnetic radiation EMR $\lambda_{max}$ and EMR $\lambda_{min}$, in certain embodiments when the sample fluid is substantially same as the reference fluid, and $L_{sample} = L_{ref} = L$, the sample fluid and the reference fluid may be irradiated only once by the EMR $\lambda_{max}$ and the difference between the change in the temperature of the sample fluid and the reference fluid due to irradiation of the EMR $\lambda_{max}$ may be used to monitor the gas of interest. For example, the concentration of the gas of interest by irradiating only EMR $\lambda_{max}$ in the sample fluid and the reference fluid with a precondition that the sample fluid is to the same as the reference fluid may be determined using the following equation (8)

$$\Delta T_4 \sim \alpha_{gas} c_{gas} L \quad (8)$$

wherein $\Delta T_4$ is a difference between the change in the temperature of the sample fluid and the change in temperature of the reference fluid due to irradiation of the EMR $\lambda_{max}$. Accordingly, in one embodiment, when the sample fluid is the same as the reference fluid (notwithstanding that the reference fluid does not contain the gas of interest), the concentration of the gas of interest may be determined based upon the difference between the change in the temperature of the sample fluid and the change in the temperature of the reference fluid due to irradiation of the EMR $\lambda_{max}$, an extinction coefficient of the gas of interest and the length of the container that contains the sample fluid.

It is further noted that in certain embodiments, a sample fluid is similar to a reference fluid (irrespective of the presence or absence of the gas of interest in the reference fluid). In such embodiment, when the sample fluid is similar to the reference fluid, the sample fluid is irradiated by electromagnetic radiation that has a first wavelength range, and the reference fluid is irradiated by electromagnetic radiation that has a second wavelength range. In one embodiment, the sample fluid is similar to the reference fluid when the absorbance of the reference fluid is within ±10% of the absorbance of the sample fluid in the measurement wavelength range. As previously noted, the first wavelength range corresponds to a spectral absorption peak ($\lambda_{max}$) of the gas of interest, and the second wavelength range corresponds to a spectral absorption valley ($\lambda_{min}$) of the gas of interest. The irradiation of the first wavelength range ($\lambda_{max}$) results in a first time temperature change of the sample fluid, and the irradiation of the second wavelength range results in a first time temperature change of the reference fluid. A first difference between the first time temperature of the sample fluid and the first time temperature change of the second fluid is determined/generated. Furthermore, the second wavelength range ($\lambda_{min}$) is irradiated into the sample fluid and the reference fluid. The irradiation of the second wavelength range results in a second time temperature change of the sample fluid and a second time temperature of the reference fluid. A second difference between the second time temperature change of the sample fluid and a second time temperature change of the reference fluid is determined. The first difference and the second difference is used to monitor the gas of interest and determine a concentration of the gas of interest.

FIG. 4 is a flowchart of a method 400 for removing noise introduced in a temperature signal or a change in the temperature signal of a sample fluid or a reference fluid due to environment temperature, in accordance with one embodiment of the present techniques. In one embodiment, the method 400 may be used to remove noise from the signal 38 (see FIG. 1) that is representative of the difference in the change in the temperatures of the sample fluid 16 and the reference fluid 18. In one embodiment, the noise may be removed by the processing subsystem 42 (see FIG. 1).

In the presently contemplated configuration, reference numeral 402 is representative of a signal that represents a difference in a change in the temperatures of a reference fluid and a sample fluid. For example, the signal 402 is the signal 38 (see FIG. 1). In certain embodiments, the signal 402 may be a signal representation of the first time temperature change of the sample fluid $\Delta T_{sample(1)}$, the first time temperature change of the reference fluid $\Delta T_{ref(1)}$, a first difference $\Delta T_1$, the second time temperature change of the sample fluid $\Delta T_{sample(2)}$, the second time temperature change of the reference fluid $\Delta T_{ref(2)}$ and the second difference $\Delta T_2$, as referred to in FIG. 3. The signal 402, for example, may be a signal 502 as shown in FIG. 5.

At 404, a start point $p_{start}$ and an end point $p_{end}$ are located to identify a trend change in the temperature of the signal 402. The start point $p_{start}$ and an end point $p_{end}$, for example, may be identified using a wavelet decomposition technique. Exemplary start point $p_{start}$ 504 and end point $p_{end}$ 506 in the signal 502 are shown in FIG. 5. The signal 502 shows a change in temperature of a sample fluid at different time stamps. As shown in the signal 502, the temperature of the sample fluid starts increasing at the start point $p_{start}$ 504, and the temperature starts decreasing at the end point $p_{end}$ 506.

Referring back to FIG. 4, at 406, a baseline signal $y_{base}$ may be determined based upon the signal 402, the start point $p_{start}$ and the end point $p_{end}$. Particularly, the baseline signal $y_{base}$ is generated by removing data points from the signal 402 that fall after the start point $p_{start}$ and before the end point $p_{end}$. In other words, the baseline signal $y_{base}$ is generated by removing the data points that show a change in temperature in the signal 402. For example, as shown in FIG. 5, a baseline signal $y_{base}$ corresponding to the signal 502 is generated by removing data points that fall in a region 507 after the start point $p_{start}$ and before the end point $p_{end}$. In one embodiment, the baseline signal $y_{base}$ may be represented by the following equation (9):

$$y_{base} = y(1:p_{start},p_{end}:\text{end}) \qquad (9)$$

wherein y is the signal 402, 502, $y_{base}$ is a baseline signal corresponding to the temperature change signal y, $p_{start}$ is a start point in the temperature change signal, $p_{end}$ is an end point in the temperature change signal y.

Referring back to FIG. 4, at 410 a combined signal X is generated based upon a plurality of environmental temperature signals 408 and the baseline signal $y_{base}$. Particularly, the combined signal X is generated by combining the environmental temperature signals 408 such that the base of the combined signal matches the baseline signal $y_{base}$. The combined signal X, for example, may be generated by applying linear regression on the environmental signals 408 to match the baseline signal $y_{base}$. The environmental temperature signals 408, for example, may be generated by the sensors 44, 46, 48, 50, 52 referred to in FIG. 1.

Subsequently at 412, a baseline trend signal is generated by applying a wavelet decomposition method to the combined signal X. An exemplary baseline trend signal 509 corresponding to the environmental signals 408 is shown in FIG. 5. Furthermore, at 414, an intermediate signal is generated based upon the baseline trend signal and the change in temperature signal 402. The intermediate signal, for example is generated by subtracting the baseline trend signal from the signal 402. For example, in FIG. 5 an intermediate signal 510 is generated by subtracting the baseline trend signal 509 from the signal 502. It is noted that subtraction of the baseline trend signal 509 from the signal 502 removes drift 512 from the signal 502 to generate the intermediate signal 510. The drift 512, for example, is a long term error introduced in the change in temperature signal 502 due to environment temperature.

Referring back to FIG. 4, at 415 a wavelet decomposition technique is applied to a portion of the intermediate signal to generate an approximate signal. Particularly, wavelet decomposition is applied to a portion of the intermediate signal that lies between the start point $p_{start}$ and the end point $p_{end}$. For, example, in FIG. 5, wavelet decomposition is applied to a portion of the intermediate signal 510 that lies between the start point $p_{start}$ and the end point $p_{end}$ to generate an approximate signal 511.

Subsequently, at 416, oscillations trend is determined based upon the intermediate and the approximate signal. For example, the oscillations trend is determined by subtracting the approximate signal from the intermediate signal. The oscillations trend represents short term or local variability in the signal 402, therefore the oscillations trend is also present in the intermediate signal, due to the environment temperature. An exemplary oscillations trend 514 corresponding to the intermediate signal 510 and the approximate signal 511 is shown in FIG. 5.

Furthermore, at 417, an environmental oscillations signal is determined based upon the combined signal X and the baseline trend signal. For example, the environmental oscillations signal is generated by subtracting the baseline trend signal from the combined signal X. An exemplary environmental oscillations signal 515 is shown in FIG. 5.

Subsequently, at 418, a residual signal is generated by filtering the oscillations trend signal using the environmental oscillations signal. For example, in FIG. 5, a residual signal is generated by filtering the oscillations trend signal 514 using the environmental oscillations signal 515. Furthermore at 420, the residual signal and the approximate signal are combined to generate a final signal. The final signal contains minimal noise due to drift and oscillations. An exemplary final signal 516 that is generated by removing drift and oscillations from the temperatures change signal 502 is shown in FIG. 5.

In certain embodiments, white noise may be removed from the final signal at 422 by using various techniques, such as, average filtering method, moving average filtering method, and the like. In this example, the removal of the white noise from the final signal results in generation of a white noise corrected final signal. An exemplary white noise corrected signal 518 that is generated by using a moving average filtering technique on the final signal 516 is shown in FIG. 5.

Subsequently, in certain embodiments, at 424 a noise corrected signal may be generated. The noise corrected, for example, may be generated by fitting a curve on the white noise corrected final signal. For example, in FIG. 5, a curve is fitted on the white noise corrected signal 518 to generate a noise corrected signal 520. The noise corrected signal, for example, may be used to monitor and determine concentration of a gas of interest in a sample fluid.

The present systems and techniques provide a direct (in-oil/fluid) approach for monitoring dissolved gases in a fluid without extracting gases from the fluid unlike known methods and devices. The present systems and techniques selectively determine individual gases and their concentrations in the fluid, for example in dielectric oils used in transformers. Furthermore, the present systems and techniques monitor and determine the concentration of the dissolved gases even when the dissolved gases are dissolved in a substantially non-transparent fluid. The device explained with reference to FIG. 1 is small and compact in one embodiment, and thus is suitable for use on-site. In other words, the device is field deployable, and can be employed near a system such as transformer for periodic gas detection analysis.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A system, comprising:
   at least one source for irradiating electromagnetic radiation into a sample fluid and a reference fluid resulting in a change in a temperature of the sample fluid and a change in a temperature of the reference fluid; and
   a processing subsystem that monitors and determines a concentration of a gas of interest dissolved in the sample fluid based upon a difference between the change in the temperature of the sample fluid and the change in the temperature of the reference fluid,
   wherein the reference fluid does not contain the gas of interest, and the electromagnetic radiation has a wavelength range corresponding to a spectral absorption range of the gas of interest.

2. The system claim of claim 1, wherein the wavelength range corresponding to the spectral absorption range is a spectral absorption peak of the gas of interest.

3. The system of claim 1, wherein the source simultaneously irradiates a first portion of the electromagnetic radiation into the sample fluid and a second portion of the electromagnetic radiation into the reference fluid.

4. The system of claim 1, further comprising:
a first container that contains the sample fluid to be tested for the determination of the gas of interest dissolved in the sample fluid; and a second container that contains the reference fluid.

5. The system of claim 4, further comprising a plurality of sensors located in the first container and the second container, wherein the plurality of sensors generate signals that are representative of the change in the temperature of the sample fluid and the change in the temperature of the reference fluid.

6. The system of claim 5, wherein the first container and the second container are arranged in a differential measurement arrangement to generate the difference between the change in the temperature of the sample fluid and the change in the temperature of the reference fluid based upon the signals representative of the change in the temperature of the sample fluid and the change in the temperature of the reference fluid.

7. The system of claim 4, further comprising one or more sensors that are in an operational communication with the processing subsystem, wherein the sensors generate signals that are representative of an environment temperature proximate the first container and the second container.

8. The system of claim 7, wherein the processing subsystem is further configured to remove noise from the change in the temperature of the sample fluid, the change in the temperature of the reference fluid, or the difference between the change in the temperature of the sample fluid and the change in the temperature of the sample fluid based upon the environment temperature.

9. The system of claim 8, wherein the processing subsystem is configured to remove the noise by applying a wavelet decomposition technique or a low pass filtering technique, an adaptive filtering technique, a moving average technique or any other higher order smoothing filters, or combination thereof on the change in the temperature of the sample fluid, the change in the temperature of the reference fluid, or the difference between the change in the temperature of the sample fluid and change in the temperature of the sample fluid.

10. The system of claim 1, wherein the processing subsystem determines the concentration of the gas of interest without extracting the gas of interest from the sample fluid.

11. The system of claim 1, wherein the sample fluid is substantially non-transparent or substantially transparent.

12. The system of claim 1, wherein the sample fluid is substantially same as the reference fluid.

13. The system of claim 1, wherein the wavelength range comprises:
a first wavelength range that corresponds to a spectral absorption peak of the gas of interest; and
a second wavelength range that corresponds to a spectral absorption valley of the gas of interest.

14. The system of claim 13, wherein the sample fluid is substantially similar to the reference fluid.

15. A system, comprising:
a first container containing a sample fluid used to determine presence of a gas of interest;
a second container containing a reference fluid that does not contain a significant amount of the gas of interest;
a source for producing electromagnetic radiation;
an optical arrangement that splits the electromagnetic radiations into a first portion of the electromagnetic radiation and a second portion of the electromagnetic radiation, and directs the first portion of the electromagnetic radiation into the sample fluid and the second portion of the electromagnetic radiation into the reference fluid to change the temperature of the sample fluid and change the temperature of the reference fluid;
a plurality of sensing devices that generate signals that are representative of the change in the temperature of the sample fluid and the change in the temperature of the reference fluid; and
a processing subsystem that determines the presence and concentration of the gas of interest in the sample fluid based upon a difference between the change in the temperature of the sample fluid and the change in the temperature of the reference fluid.

16. The system of claim 15, wherein the sample fluid is substantially non-transparent or substantially transparent.

17. The system of claim 15, wherein the sample fluid is substantially same as the reference fluid.

18. The system of claim 15, wherein at least one sensing device is in an operational communication with the processing subsystem, wherein the at least one sensing device generates signals that are representative of an environment temperature proximate the first container and the second container.

19. The system of claim 15, wherein the processing subsystem is further configured to remove noise from the change in the temperature of the sample fluid, the change in the temperature of the reference fluid, or the difference between the change in the temperature of the sample fluid and the change in the temperature of the sample fluid based upon the environment temperature.

20. The system of claim 19, wherein the processing subsystem is configured to remove the noise by applying a wavelet decomposition technique or a low pass filtering technique.

* * * * *